US008029451B2

(12) United States Patent
Meyer et al.

(10) Patent No.: US 8,029,451 B2
(45) Date of Patent: Oct. 4, 2011

(54) COMPRESSION SLEEVE HAVING AIR CONDUITS

(75) Inventors: Ann Meyer, Shrewsbury, MA (US); Mark A. Vess, Hanson, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 276 days.

(21) Appl. No.: 12/251,004

(22) Filed: Oct. 14, 2008

(65) Prior Publication Data

US 2009/0062703 A1 Mar. 5, 2009

Related U.S. Application Data

(63) Continuation-in-part of application No. 11/299,488, filed on Dec. 12, 2005, now Pat. No. 7,442,175.

(51) Int. Cl.
*A61F 5/00* (2006.01)

(52) U.S. Cl. ................................ 602/13; 602/23; 602/27

(58) Field of Classification Search .................... 602/13, 602/20–27; 128/882, DIG. 20
See application file for complete search history.

(56) References Cited

U.S. PATENT DOCUMENTS 908,959 A 1/1909 Cooke
910,689 A 1/1909 Kelly et al.
1,510,482 A 10/1924 Kramer
1,608,239 A 11/1926 Rosett
2,199,408 A 5/1940 La Liberte
2,489,388 A 11/1949 Rubin
2,533,504 A 12/1950 Poor
2,638,915 A 5/1953 Mitchell
2,676,587 A 4/1954 Corcoran
2,694,395 A 11/1954 Brown
2,880,721 A 4/1959 Corcoran
2,896,612 A 7/1959 Bates et al.
2,998,817 A 9/1961 Armstrong
3,164,152 A 1/1965 Vere Nicoll
3,245,405 A 4/1966 Gardner
3,288,132 A 11/1966 Meredith
3,351,055 A 11/1967 Gottfried
3,454,010 A 7/1969 Lilligren et al.
3,469,769 A 9/1969 Guenther
3,473,527 A 10/1969 Spiro
3,561,435 A 2/1971 Nicholson
3,568,227 A 3/1971 Dunham
3,606,880 A 9/1971 Ogle, Jr.
3,701,173 A 10/1972 Whitney
(Continued)

FOREIGN PATENT DOCUMENTS

DE 19846922 A1 4/2000
(Continued)

OTHER PUBLICATIONS

Mittelman, Jonathan S., MD: "Effectiveness of Leg Compression in Preventing Venous Stasis", The American Journal of Surgery, Dec. 1982, p. 611-613, vol. 144, No. 6, Elsevier Publ., Bridgewater, NJ, USA.

(Continued)

*Primary Examiner* — Michael A. Brown
(74) *Attorney, Agent, or Firm* — Thomas M. Johnston, Esq.

(57) ABSTRACT

A compression sleeve is described as having a first sheet, a second sheet attached to said first sheet and defining at least one inflatable section, and at least one conduit disposed within the boundary of the least one of said inflatable sections.

6 Claims, 10 Drawing Sheets

U.S. PATENT DOCUMENTS

| | | | | |
|---|---|---|---|---|
| 3,728,875 | A | 4/1973 | Hartigan et al. | |
| 3,760,795 | A | 9/1973 | Adelhed | |
| 3,771,519 | A | 11/1973 | Haake | |
| 3,786,805 | A | 1/1974 | Tourin | |
| 3,824,992 | A | 7/1974 | Nicholson et al. | |
| 3,826,249 | A | 7/1974 | Lee et al. | |
| 3,862,629 | A | 1/1975 | Rotta | |
| 3,868,952 | A | 3/1975 | Hatton | |
| 3,877,426 | A | 4/1975 | Nirschl | |
| 3,878,839 | A | 4/1975 | Norton et al. | |
| 3,899,210 | A | 8/1975 | Samhammer et al. | |
| 3,901,221 | A | 8/1975 | Nicholson et al. | |
| 3,906,937 | A | 9/1975 | Aronson | |
| 3,920,006 | A | 11/1975 | Lapidus | |
| D239,981 | S | 5/1976 | Arbuck et al. | |
| 3,955,565 | A | 5/1976 | Johnson, Jr. | |
| 4,013,069 | A | 3/1977 | Hasty | |
| 4,029,087 | A | 6/1977 | Dye et al. | |
| 4,030,488 | A | 6/1977 | Hasty | |
| 4,054,129 | A | 10/1977 | Byars et al. | |
| 4,066,084 | A | 1/1978 | Tillander | |
| 4,076,022 | A | 2/1978 | Walker | |
| 4,091,804 | A | 5/1978 | Hasty | |
| 4,146,021 | A | 3/1979 | Brosseau et al. | |
| 4,149,529 | A | 4/1979 | Copeland et al. | |
| 4,149,541 | A | 4/1979 | Gammons et al. | |
| 4,153,050 | A | 5/1979 | Bishop et al. | |
| 4,156,425 | A | 5/1979 | Arkans | |
| 4,198,961 | A | 4/1980 | Arkans | |
| 4,202,312 | A | 5/1980 | Mori et al. | |
| 4,202,325 | A | 5/1980 | Villari et al. | |
| 4,206,751 | A | 6/1980 | Schneider | |
| 4,207,875 | A | 6/1980 | Arkans | |
| 4,207,876 | A | 6/1980 | Annis | |
| 4,219,892 | A | 9/1980 | Rigdon | |
| 4,253,449 | A | 3/1981 | Arkans et al. | |
| 4,267,611 | A | 5/1981 | Agulnick | |
| 4,270,527 | A | 6/1981 | Peters et al. | |
| 4,280,485 | A | 7/1981 | Arkans | |
| 4,294,240 | A | 10/1981 | Thill | |
| 4,300,245 | A | 11/1981 | Saunders | |
| 4,308,862 | A | 1/1982 | Kalmar | |
| 4,311,135 | A | 1/1982 | Brueckner et al. | |
| 4,320,746 | A | 3/1982 | Arkans et al. | |
| 4,351,872 | A | 9/1982 | Brosseau et al. | |
| 4,355,632 | A | 10/1982 | Sandman | |
| 4,363,125 | A | 12/1982 | Brewer et al. | |
| 4,372,297 | A * | 2/1983 | Perlin | 601/151 |
| 4,375,217 | A | 3/1983 | Arkans | |
| 4,379,217 | A | 4/1983 | Youmans | |
| 4,402,312 | A | 9/1983 | Villari et al. | |
| 4,408,599 | A | 10/1983 | Mummert | |
| 4,417,587 | A | 11/1983 | Ichinomiya et al. | |
| 4,437,269 | A | 3/1984 | Shaw | |
| 4,442,834 | A | 4/1984 | Tucker et al. | |
| 4,445,505 | A | 5/1984 | Labour et al. | |
| 4,453,538 | A | 6/1984 | Whitney | |
| 4,522,197 | A | 6/1985 | Hasegawa | |
| 4,531,516 | A | 7/1985 | Poole et al. | |
| 4,547,906 | A | 10/1985 | Nishida et al. | |
| 4,547,919 | A | 10/1985 | Wang | |
| 4,552,821 | A | 11/1985 | Gibbard et al. | |
| 4,580,816 | A | 4/1986 | Campbell et al. | |
| 4,593,692 | A | 6/1986 | Flowers | |
| 4,597,384 | A | 7/1986 | Whitney | |
| 4,614,179 | A | 9/1986 | Gardner et al. | |
| 4,614,180 | A | 9/1986 | Gardner et al. | |
| 4,624,244 | A | 11/1986 | Taheri | |
| 4,624,248 | A | 11/1986 | Poole et al. | |
| 4,650,452 | A | 3/1987 | Jensen | |
| 4,657,003 | A | 4/1987 | Wirtz | |
| 4,682,588 | A | 7/1987 | Curlee | |
| 4,696,289 | A | 9/1987 | Gardner et al. | |
| 4,699,424 | A | 10/1987 | Andres et al. | |
| 4,702,232 | A | 10/1987 | Gardner et al. | |
| 4,703,750 | A | 11/1987 | Sebastian et al. | |
| 4,706,658 | A | 11/1987 | Cronin | |
| 4,721,101 | A | 1/1988 | Gardner et al. | |
| 4,722,332 | A | 2/1988 | Saggers | |
| 4,730,606 | A | 3/1988 | Leininger | |
| 4,762,121 | A | 8/1988 | Shienfeld | |
| 4,773,397 | A | 9/1988 | Wright et al. | |
| 4,805,620 | A | 2/1989 | Meistrell | |
| 4,809,684 | A | 3/1989 | Gardner et al. | |
| 4,827,912 | A | 5/1989 | Carrington et al. | |
| 4,832,010 | A | 5/1989 | Lerman | |
| RE32,939 | E | 6/1989 | Gardner et al. | |
| RE32,940 | E | 6/1989 | Gardner et al. | |
| 4,836,194 | A | 6/1989 | Sebastian et al. | |
| 4,836,691 | A | 6/1989 | Suzuki et al. | |
| 4,841,956 | A | 6/1989 | Gardner et al. | |
| D302,301 | S | 7/1989 | Robinette-Lehman | |
| 4,846,160 | A | 7/1989 | Gardner et al. | |
| 4,846,189 | A | 7/1989 | Sun | |
| 4,869,265 | A | 9/1989 | McEwen | |
| 4,872,448 | A | 10/1989 | Johnson, Jr. | |
| 4,876,788 | A | 10/1989 | Steer et al. | |
| 4,883,073 | A | 11/1989 | Aziz | |
| 4,886,053 | A | 12/1989 | Neal | |
| 4,898,160 | A | 2/1990 | Brownlee | |
| 4,938,207 | A | 7/1990 | Vargo | |
| 4,938,208 | A | 7/1990 | Dye | |
| 4,938,226 | A | 7/1990 | Danielsson et al. | |
| 4,945,571 | A | 8/1990 | Calvert | |
| 4,947,834 | A | 8/1990 | Kartheus et al. | |
| 4,957,105 | A | 9/1990 | Kurth | |
| 4,960,115 | A | 10/1990 | Ranciato | |
| 4,964,402 | A | 10/1990 | Grim et al. | |
| 4,979,953 | A | 12/1990 | Spence | |
| 4,989,273 | A | 2/1991 | Cromartie | |
| 5,007,411 | A | 4/1991 | Dye | |
| 5,014,681 | A | 5/1991 | Neeman et al. | |
| 5,022,387 | A | 6/1991 | Hasty | |
| 5,031,604 | A | 7/1991 | Dye | |
| 5,048,536 | A | 9/1991 | McEwen | |
| 5,052,377 | A | 10/1991 | Frajdenrajch | |
| 5,062,414 | A | 11/1991 | Grim | |
| 5,069,219 | A | 12/1991 | Knoblich | |
| 5,080,951 | A | 1/1992 | Guthrie | |
| 5,109,832 | A | 5/1992 | Proctor et al. | |
| 5,117,812 | A | 6/1992 | McWhorter | |
| 5,120,300 | A | 6/1992 | Shaw | |
| 5,135,473 | A | 8/1992 | Epler et al. | |
| 5,139,476 | A | 8/1992 | Peters | |
| 5,146,932 | A | 9/1992 | McCabe | |
| 5,156,629 | A | 10/1992 | Shane et al. | |
| 5,158,541 | A | 10/1992 | McCurley | |
| 5,168,576 | A | 12/1992 | Krent et al. | |
| 5,172,689 | A | 12/1992 | Wright | |
| D332,495 | S | 1/1993 | Lake | |
| 5,179,941 | A | 1/1993 | Siemssen et al. | |
| 5,181,522 | A | 1/1993 | McEwen | |
| 5,186,163 | A | 2/1993 | Dye | |
| 5,193,549 | A | 3/1993 | Bellin et al. | |
| 5,211,162 | A | 5/1993 | Gillen, Jr. et al. | |
| 5,226,245 | A | 7/1993 | Lamont | |
| 5,226,564 | A | 7/1993 | Steer et al. | |
| 5,230,335 | A | 7/1993 | Johnson, Jr. et al. | |
| 5,245,990 | A | 9/1993 | Bertinin | |
| 5,259,397 | A | 11/1993 | McCabe | |
| 5,263,473 | A | 11/1993 | McWhorter | |
| 5,277,695 | A | 1/1994 | Johnson, Jr. et al. | |
| 5,277,697 | A | 1/1994 | France et al. | |
| 5,314,455 | A | 5/1994 | Johnson, Jr. et al. | |
| 5,334,135 | A | 8/1994 | Grim et al. | |
| 5,342,285 | A | 8/1994 | Dye | |
| 5,354,260 | A | 10/1994 | Cook | |
| 5,378,224 | A | 1/1995 | Billotti | |
| 5,383,894 | A | 1/1995 | Dye | |
| 5,383,919 | A | 1/1995 | Kelly et al. | |
| 5,385,538 | A | 1/1995 | Mann | |
| 5,389,065 | A | 2/1995 | Johnson, Jr. | |
| 5,391,141 | A | 2/1995 | Hamilton | |
| 5,399,153 | A | 3/1995 | Caprio, Jr. et al. | |
| 5,403,265 | A | 4/1995 | Berguer et al. | |
| 5,407,421 | A | 4/1995 | Goldsmith | |
| D358,216 | S | 5/1995 | Dye | |

5,413,142 A 5/1995 Johnson et al.
5,413,582 A 5/1995 Eaton
5,419,757 A 5/1995 Daneshvar
5,425,701 A 6/1995 Oster et al.
5,435,009 A 7/1995 Schild et al.
5,437,595 A 8/1995 Smith
5,437,610 A 8/1995 Cariapa et al.
5,441,533 A 8/1995 Johnson et al.
5,443,440 A 8/1995 Tumey et al.
5,449,341 A 9/1995 Harris
5,449,379 A 9/1995 Hadtke
5,450,858 A 9/1995 Zablotsky et al.
5,451,201 A 9/1995 Prengler
5,453,081 A 9/1995 Hansen
5,458,265 A 10/1995 Hester et al.
5,462,517 A 10/1995 Mann
5,466,250 A 11/1995 Johnson, Jr. et al.
5,470,156 A 11/1995 May
5,478,119 A 12/1995 Dye
5,489,252 A 2/1996 May
5,489,259 A 2/1996 Jacobs et al.
5,496,262 A 3/1996 Johnson, Jr. et al.
5,503,620 A 4/1996 Danzger
5,511,552 A 4/1996 Johnson
5,513,658 A 5/1996 Goseki
5,514,081 A 5/1996 Mann
5,514,155 A 5/1996 Daneshvar
5,527,267 A 6/1996 Billotti
5,554,105 A 9/1996 Taylor
D376,013 S 11/1996 Sandman et al.
5,575,762 A 11/1996 Peeler et al.
5,578,055 A 11/1996 McEwen
5,584,798 A 12/1996 Fox
5,588,954 A 12/1996 Ribando et al.
5,588,955 A 12/1996 Johnson, Jr. et al.
5,588,956 A 12/1996 Billotti
5,591,200 A 1/1997 Cone et al.
5,591,337 A 1/1997 Lynn et al.
5,603,690 A 2/1997 Barry
5,609,570 A 3/1997 Lamont
5,620,411 A 4/1997 Schumann et al.
5,626,556 A 5/1997 Tobler et al.
5,626,557 A 5/1997 Mann
5,634,889 A 6/1997 Gardner et al.
5,637,106 A 6/1997 Mitchell et al.
5,640,714 A 6/1997 Tanaka
5,649,954 A 7/1997 McEwen
5,653,244 A 8/1997 Shaw
D383,547 S 9/1997 Mason et al.
5,664,270 A 9/1997 Bell et al.
5,669,872 A 9/1997 Fox
5,674,262 A 10/1997 Tumey
5,678,558 A 10/1997 Johnson
5,695,453 A 12/1997 Neal
5,704,999 A 1/1998 Lukich et al.
5,711,757 A 1/1998 Bryant
5,717,996 A 2/1998 Feldmann
5,725,485 A 3/1998 Ribando et al.
5,728,055 A 3/1998 Sebastian
5,728,057 A 3/1998 Ouellette et al.
5,730,710 A 3/1998 Eichhorn et al.
5,741,295 A 4/1998 McEwen
5,746,213 A 5/1998 Marks
5,769,800 A 6/1998 Gelfand et al.
5,769,801 A 6/1998 Tumey et al.
5,772,880 A 6/1998 Lynn et al.
5,790,998 A 8/1998 Crescimbeni
5,795,312 A 8/1998 Dye
5,797,851 A 8/1998 Byrd
5,823,981 A 10/1998 Grim et al.
5,830,164 A 11/1998 Cone et al.
5,833,639 A 11/1998 Nunes et al.
5,840,049 A 11/1998 Tumey et al.
5,843,007 A 12/1998 McEwen et al.
D403,775 S 1/1999 Davis et al.
D405,884 S 2/1999 Roper
5,876,359 A 3/1999 Bock et al.
5,891,065 A 4/1999 Cariapa et al.
5,894,682 A 4/1999 Broz
D411,301 S 6/1999 Hampson et al.
5,916,183 A 6/1999 Reid
5,925,010 A 7/1999 Caprio, Jr.
5,926,850 A 7/1999 Han
5,931,797 A 8/1999 Tumey et al.
5,938,628 A 8/1999 Oguri et al.
5,951,502 A 9/1999 Peeler et al.
5,957,872 A 9/1999 Flick
5,966,763 A 10/1999 Thomas et al.
5,968,072 A 10/1999 Hite et al.
5,976,099 A 11/1999 Kellogg
5,976,300 A 11/1999 Buchanan et al.
5,988,704 A 11/1999 Ryhman
5,989,204 A 11/1999 Lina
5,991,654 A 11/1999 Tumey et al.
5,997,495 A 12/1999 Cook et al.
5,997,981 A 12/1999 McCormack et al.
6,001,119 A 12/1999 Hampson et al.
6,007,559 A 12/1999 Arkans
6,010,471 A 1/2000 Ben-Noon
6,021,780 A 2/2000 Darby
6,036,718 A 3/2000 Ledford et al.
6,048,326 A 4/2000 Davis et al.
6,051,016 A 4/2000 Mesaros et al.
6,062,244 A 5/2000 Arkans
6,066,217 A 5/2000 Dibble et al.
6,076,193 A 6/2000 Hood
6,080,120 A 6/2000 Sandman et al.
D428,153 S 7/2000 Davis
6,110,135 A 8/2000 Madow et al.
6,126,683 A 10/2000 Momtaheni
6,129,688 A 10/2000 Arkans
6,129,695 A 10/2000 Peters et al.
6,135,116 A 10/2000 Vogel et al.
6,145,143 A 11/2000 Hicks et al.
6,149,600 A 11/2000 Poorman-Ketchum
6,152,495 A 11/2000 Hoffmann et al.
6,152,893 A 11/2000 Pigg et al.
6,168,539 B1 1/2001 Maina
6,171,271 B1 1/2001 Hörnberg
6,179,796 B1 1/2001 Waldridge
6,197,045 B1 3/2001 Carson
6,203,510 B1 3/2001 Takeuchi et al.
6,209,159 B1 4/2001 Murphy
6,212,719 B1 4/2001 Thomas et al.
6,231,507 B1 5/2001 Zikorus et al.
6,231,532 B1 5/2001 Watson et al.
6,245,023 B1 6/2001 Clemmons
6,254,554 B1 7/2001 Turtzo
6,257,626 B1 7/2001 Campau
6,257,627 B1 7/2001 Fujiwara et al.
6,273,866 B2 8/2001 Thomas et al.
6,290,662 B1 9/2001 Morris et al.
6,290,664 B1 9/2001 Nauert
6,296,617 B1 10/2001 Peeler et al.
6,315,745 B1 11/2001 Kloecker
6,319,215 B1 11/2001 Manor et al.
6,322,530 B1 11/2001 Johnson, Jr. et al.
6,336,935 B1 1/2002 Davis et al.
6,338,723 B1 1/2002 Carpenter et al.
6,349,506 B1 2/2002 Pace et al.
6,358,219 B1 3/2002 Arkans
6,361,496 B1 3/2002 Zikorus et al.
6,368,357 B1 4/2002 Schon et al.
6,375,633 B1 4/2002 Endress et al.
6,385,778 B1 5/2002 Johnson
6,385,864 B1 5/2002 Sell, Jr. et al.
6,387,065 B1 5/2002 Tumey
6,402,879 B1 6/2002 Tawney et al.
6,421,859 B1 7/2002 Hicks et al.
6,423,053 B1 7/2002 Lee
6,436,064 B1 8/2002 Kloecker
6,440,093 B1 8/2002 McEwen et al.
6,447,460 B1 9/2002 Zheng et al.
6,447,467 B1 9/2002 Barak
6,463,934 B1 10/2002 Johnson, Jr. et al.
6,468,237 B1 10/2002 Lina
6,478,757 B1 11/2002 Barak
6,488,643 B1 12/2002 Tumey et al.

| | | | |
|---|---|---|---|
| 6,493,568 | B1 | 12/2002 | Bell et al. |
| 6,494,852 | B1 | 12/2002 | Barak et al. |
| 6,508,205 | B1 | 1/2003 | Zink |
| 6,520,926 | B2 | 2/2003 | Hall |
| 6,526,597 | B1 | 3/2003 | Shepard |
| 6,527,727 | B2 | 3/2003 | Itonaga et al. |
| 6,537,298 | B2 | 3/2003 | Dedo |
| 6,540,707 | B1 | 4/2003 | Stark et al. |
| 6,544,202 | B2 | 4/2003 | McEwen et al. |
| 6,549,748 | B2 | 4/2003 | Miura |
| 6,551,280 | B1 | 4/2003 | Knighton et al. |
| 6,554,785 | B1 * | 4/2003 | Sroufe et al. .................... 602/23 |
| 6,557,704 | B1 | 5/2003 | Randolph |
| 6,558,338 | B1 | 5/2003 | Wasserman |
| 6,589,267 | B1 | 7/2003 | Hui |
| 6,589,534 | B1 | 7/2003 | Shaul et al. |
| 6,592,534 | B1 | 7/2003 | Rutt et al. |
| 6,593,508 | B1 | 7/2003 | Harder |
| 6,598,249 | B2 | 7/2003 | Pajanacci et al. |
| D478,995 | S | 8/2003 | Cipra et al. |
| 6,616,622 | B1 | 9/2003 | Barberio |
| 6,618,859 | B1 | 9/2003 | Kadymir et al. |
| 6,629,941 | B1 | 10/2003 | Ishibashi et al. |
| 6,645,165 | B2 | 11/2003 | Waldridge et al. |
| D484,986 | S | 1/2004 | Cipra et al. |
| 6,676,614 | B1 | 1/2004 | Hansen et al. |
| 6,682,547 | B2 | 1/2004 | McEwen et al. |
| 6,685,661 | B2 | 2/2004 | Peled |
| 6,719,711 | B1 | 4/2004 | Islava |
| 6,726,641 | B2 | 4/2004 | Chiang et al. |
| 6,746,470 | B2 | 6/2004 | McEwen et al. |
| 6,757,516 | B2 | 6/2004 | Miura |
| 6,762,337 | B2 | 7/2004 | Boukanov et al. |
| 6,762,338 | B2 | 7/2004 | Harder |
| 6,842,915 | B2 | 1/2005 | Turner et al. |
| 6,846,294 | B2 | 1/2005 | Rastegar et al. |
| 6,846,295 | B1 | 1/2005 | Ben-Nun |
| 6,849,057 | B2 | 2/2005 | Satou et al. |
| 6,852,089 | B2 | 2/2005 | Kloecker et al. |
| 6,860,862 | B2 | 3/2005 | Waldridge et al. |
| 6,862,989 | B2 | 3/2005 | Belanger et al. |
| 6,866,636 | B2 | 3/2005 | Inoue et al. |
| 6,869,409 | B2 | 3/2005 | Rothman et al. |
| D506,553 | S | 6/2005 | Tesluk |
| 6,945,944 | B2 | 9/2005 | Kuiper et al. |
| D510,626 | S | 10/2005 | Krahner et al. |
| 6,966,884 | B2 | 11/2005 | Waldridge et al. |
| 6,984,215 | B2 | 1/2006 | Shah |
| 6,991,613 | B2 | 1/2006 | Sensabaugh |
| 7,011,640 | B2 | 3/2006 | Patterson et al. |
| 7,022,096 | B1 | 4/2006 | Alfieri |
| 7,041,074 | B1 | 5/2006 | Averianov et al. |
| 7,044,924 | B1 | 5/2006 | Roth et al. |
| 7,048,703 | B2 | 5/2006 | Riach |
| 7,063,676 | B2 | 6/2006 | Barak et al. |
| 7,104,967 | B2 | 9/2006 | Rothman et al. |
| D533,668 | S | 12/2006 | Brown |
| 7,166,077 | B2 | 1/2007 | Millay et al. |
| 7,214,202 | B1 | 5/2007 | Vogel et al. |
| 7,217,249 | B2 | 5/2007 | Scott |
| D545,972 | S | 7/2007 | Wierenga et al. |
| 7,237,272 | B2 | 7/2007 | Botcher |
| 7,238,080 | B2 | 7/2007 | Gimble |
| 7,244,483 | B2 | 7/2007 | Tawney et al. |
| 7,258,676 | B2 | 8/2007 | Calderon et al. |
| D550,367 | S | 9/2007 | Nash |
| 7,276,037 | B2 | 10/2007 | Ravikumar |
| 7,276,039 | B2 | 10/2007 | Garelick et al. |
| 7,278,980 | B1 | 10/2007 | Garelick et al. |
| 7,282,038 | B2 * | 10/2007 | Gillis et al. .................. 601/151 |
| 7,285,103 | B2 | 10/2007 | Nathanson |
| 7,288,076 | B2 | 10/2007 | Grim et al. |
| 7,297,128 | B2 | 11/2007 | Binder et al. |
| 7,303,539 | B2 | 12/2007 | Binder et al. |
| 7,306,568 | B2 | 12/2007 | Diana |
| 7,310,847 | B2 | 12/2007 | Bolkan et al. |
| 7,318,812 | B2 | 1/2008 | Taylor et al. |
| D562,461 | S | 2/2008 | Nash |
| D562,462 | S | 2/2008 | Muir et al. |
| 7,326,227 | B2 | 2/2008 | Dedo et al. |
| 7,329,232 | B2 | 2/2008 | Lipshaw et al. |
| 7,351,217 | B2 | 4/2008 | Scherpenborg |
| 7,353,770 | B2 | 4/2008 | Sanguinetti |
| 7,354,410 | B2 | 4/2008 | Perry et al. |
| 7,354,411 | B2 | 4/2008 | Perry et al. |
| 7,374,550 | B2 | 5/2008 | Hansen et al. |
| D577,124 | S | 9/2008 | Freeland et al. |
| 7,424,936 | B2 | 9/2008 | McClellan |
| 7,465,283 | B2 | 12/2008 | Grim et al. |
| 7,468,048 | B2 | 12/2008 | Meehan |
| 7,473,816 | B2 | 1/2009 | Hall |
| D594,561 | S | 6/2009 | Freeland et al. |
| 7,543,399 | B2 | 6/2009 | Kilgore et al. |
| 7,559,908 | B2 | 7/2009 | Ravikumar |
| 7,578,799 | B2 | 8/2009 | Thorsteinsson et al. |
| 7,591,796 | B1 | 9/2009 | Barak et al. |
| 7,591,797 | B2 | 9/2009 | Hakonson et al. |
| 7,597,675 | B2 | 10/2009 | Ingimundarson et al. |
| 7,615,027 | B2 | 11/2009 | Nordt, III et al. |
| 7,618,389 | B2 | 11/2009 | Nordt, III et al. |
| 7,625,348 | B2 | 12/2009 | Young et al. |
| 7,637,879 | B2 | 12/2009 | Barak et al. |
| D608,006 | S | 1/2010 | Avitable et al. |
| 7,654,117 | B2 | 2/2010 | Barnett |
| 7,691,084 | B2 * | 4/2010 | Knighton et al. ............. 604/133 |
| 7,748,090 | B2 | 7/2010 | Seth et al. |
| 2001/0018564 | A1 | 8/2001 | Manor et al. |
| 2002/0068886 | A1 | 6/2002 | Lin |
| 2002/0069731 | A1 | 6/2002 | Soucy |
| 2002/0115949 | A1 | 8/2002 | Kuslich et al. |
| 2003/0018313 | A1 | 1/2003 | Tanzer et al. |
| 2003/0083605 | A1 | 5/2003 | Edmund |
| 2003/0139255 | A1 | 7/2003 | Lina |
| 2003/0199922 | A1 | 10/2003 | Buckman |
| 2004/0010212 | A1 | 1/2004 | Kuiper et al. |
| 2004/0039317 | A1 | 2/2004 | Souney et al. |
| 2004/0039413 | A1 | 2/2004 | Akerfeldt et al. |
| 2004/0054306 | A1 | 3/2004 | Roth et al. |
| 2004/0068290 | A1 | 4/2004 | Bates et al. |
| 2004/0097860 | A1 | 5/2004 | Tauber |
| 2004/0158283 | A1 | 8/2004 | Shook et al. |
| 2004/0158285 | A1 | 8/2004 | Pillai |
| 2004/0176715 | A1 | 9/2004 | Nelson |
| 2004/0181156 | A1 | 9/2004 | Kingsford et al. |
| 2004/0181254 | A1 | 9/2004 | Choi et al. |
| 2004/0199090 | A1 | 10/2004 | Sanders et al. |
| 2004/0210167 | A1 | 10/2004 | Webster |
| 2004/0236258 | A1 | 11/2004 | Burns et al. |
| 2005/0070828 | A1 | 3/2005 | Hampson et al. |
| 2005/0143683 | A1 | 6/2005 | Waldridge et al. |
| 2005/0154336 | A1 | 7/2005 | Kloecker et al. |
| 2005/0187501 | A1 | 8/2005 | Ravikumar |
| 2005/0187503 | A1 | 8/2005 | Tordella et al. |
| 2005/0209545 | A1 | 9/2005 | Farrow et al. |
| 2005/0242315 | A1 | 11/2005 | Lund |
| 2005/0261617 | A1 | 11/2005 | Hall |
| 2006/0010574 | A1 | 1/2006 | Linnane et al. |
| 2006/0020236 | A1 | 1/2006 | Ben-Nun |
| 2006/0135894 | A1 | 6/2006 | G. Linnane et al. |
| 2006/0142719 | A1 | 6/2006 | Vogt et al. |
| 2006/0161081 | A1 | 7/2006 | Barak et al. |
| 2006/0189907 | A1 | 8/2006 | Pick et al. |
| 2006/0211965 | A1 | 9/2006 | Horn et al. |
| 2007/0038167 | A1 | 2/2007 | Tabron et al. |
| 2007/0088239 | A1 | 4/2007 | Roth et al. |
| 2007/0129658 | A1 | 6/2007 | Hampson et al. |
| 2007/0135742 | A1 | 6/2007 | Meyer et al. |
| 2007/0135743 | A1 | 6/2007 | Meyer |
| 2007/0135835 | A1 | 6/2007 | McEwen et al. |
| 2007/0135836 | A1 | 6/2007 | McEwen et al. |
| 2007/0161933 | A1 | 7/2007 | Ravikumar |
| 2007/0167892 | A1 | 7/2007 | Gramza et al. |
| 2007/0167895 | A1 | 7/2007 | Gramza et al. |
| 2007/0179416 | A1 | 8/2007 | Obrien et al. |
| 2007/0197943 | A1 | 8/2007 | Hakonson et al. |
| 2007/0197944 | A1 | 8/2007 | Bruce et al. |
| 2007/0197947 | A1 | 8/2007 | Scott |
| 2007/0219580 | A1 | 9/2007 | McEwen et al. |

| | | | |
|---|---|---|---|
| 2007/0244506 | A1 | 10/2007 | McEwen et al. |
| 2007/0260162 | A1 | 11/2007 | Meyer et al. |
| 2007/0276310 | A1 | 11/2007 | Lipshaw et al. |
| 2007/0276311 | A1 | 11/2007 | Wieringa et al. |
| 2007/0282233 | A1 | 12/2007 | Meyer et al. |
| 2008/0000477 | A1 | 1/2008 | Huster et al. |
| 2008/0004555 | A1 | 1/2008 | Reis et al. |
| 2008/0004560 | A1 | 1/2008 | Miskie |
| 2008/0021363 | A1 | 1/2008 | Fee |
| 2008/0023423 | A1 | 1/2008 | Duffy |
| 2008/0034479 | A1 | 2/2008 | Barnett |
| 2008/0039756 | A1 | 2/2008 | Thorsteinsson et al. |
| 2008/0039757 | A1 | 2/2008 | Nordt, III et al. |
| 2008/0064996 | A1 | 3/2008 | Bretl et al. |
| 2008/0071204 | A1 | 3/2008 | Linnane et al. |
| 2008/0086071 | A1 | 4/2008 | Weatherly |
| 2008/0103397 | A1 | 5/2008 | Barak |
| 2008/0103422 | A1 | 5/2008 | Perry et al. |
| 2008/0119771 | A1 | 5/2008 | Jaccard |
| 2008/0188786 | A1 | 8/2008 | Hickling |
| 2008/0208092 | A1 | 8/2008 | Sawa |
| 2008/0234615 | A1 | 9/2008 | Cook et al. |
| 2008/0243173 | A1 | 10/2008 | Thorpe |
| 2008/0245361 | A1 | 10/2008 | Brown |
| 2008/0249440 | A1 | 10/2008 | Avitable et al. |
| 2008/0249441 | A1 | 10/2008 | Avitable et al. |
| 2008/0249442 | A1 | 10/2008 | Brown et al. |
| 2008/0249443 | A1 | 10/2008 | Avitable et al. |
| 2008/0249444 | A1 | 10/2008 | Avitable et al. |
| 2008/0249447 | A1 | 10/2008 | Brown et al. |
| 2008/0249449 | A1 | 10/2008 | Brown et al. |
| 2008/0249455 | A1 | 10/2008 | Brown et al. |
| 2008/0249559 | A1 | 10/2008 | Brown et al. |
| 2008/0250551 | A1 | 10/2008 | Mazzarolo |
| 2008/0255485 | A1 | 10/2008 | Johnson et al. |
| 2008/0281351 | A1 | 11/2008 | Croushorn et al. |
| 2008/0306420 | A1 | 12/2008 | Vess |
| 2008/0312682 | A1 | 12/2008 | Shams et al. |
| 2009/0005718 | A1 | 1/2009 | Lightbourne |
| 2009/0062703 | A1 | 3/2009 | Meyer et al. |
| 2009/0064919 | A1 | 3/2009 | Greenwald |
| 2009/0076432 | A1 | 3/2009 | Winkler |
| 2009/0082708 | A1 | 3/2009 | Scott et al. |
| 2009/0099562 | A1 | 4/2009 | Ingimudarson et al. |
| 2009/0110890 | A1 | 4/2009 | Garza et al. |
| 2009/0124944 | A1 | 5/2009 | Ravikumar |
| 2009/0133446 | A1 | 5/2009 | Burrow et al. |
| 2009/0163842 | A1 | 6/2009 | Cropper |
| 2009/0171223 | A1 | 7/2009 | McEwen et al. |
| 2009/0177222 | A1 | 7/2009 | Brown et al. |
| 2009/0198261 | A1 | 8/2009 | Schweikert |
| 2009/0227917 | A1 | 9/2009 | Nardi |
| 2009/0227919 | A1 | 9/2009 | Nardi et al. |
| 2009/0227922 | A1 | 9/2009 | Nardi et al. |
| 2009/0234265 | A1 | 9/2009 | Reid et al. |
| 2009/0270910 | A1 | 10/2009 | Hargens et al. |
| 2009/0278707 | A1 | 11/2009 | Biggins et al. |
| 2009/0320174 | A1 | 12/2009 | Turner |
| 2009/0326576 | A1 | 12/2009 | Ben-Nun |
| 2010/0004575 | A1 | 1/2010 | Vess |
| 2010/0004676 | A1 | 1/2010 | McEwen et al. |
| 2010/0042026 | A1 | 2/2010 | Kloecker et al. |
| 2010/0042028 | A1 | 2/2010 | Frank et al. |

FOREIGN PATENT DOCUMENTS

| | | | |
|---|---|---|---|
| EP | 0303029 | A1 | 2/1989 |
| EP | 0408049 | A2 | 1/1991 |
| EP | 0861651 | A1 | 9/1998 |
| EP | 1468816 | A1 | 10/2004 |
| FR | 2813770 | A1 | 3/2002 |
| GB | 2061086 | A | 5/1981 |
| GB | 2178663 | A | 2/1987 |
| GB | 2183483 | A | 6/1987 |
| GB | 2313784 | A | 12/1997 |
| GB | 2373444 | A | 9/2002 |
| JP | 59218154 | A | 12/1984 |
| JP | 60135110 | U | 9/1985 |
| JP | 2002065782 | | 3/2002 |
| JP | 2004081709 | | 3/2004 |
| JP | 2005066247 | | 3/2005 |
| WO | 2005082315 | A1 | 9/2005 |
| WO | 2006083865 | A2 | 8/2006 |

OTHER PUBLICATIONS

Tyco Healthcare Kendall, SCD Response Catalog, Mar. 2000, pp. 1-2.

Tyco Healthcare Kendall, SCD Soft Sleeve Catalog, Apr. 2001, pp. 1-2.

The Kendall Company, Vascular Therapy Products Catalog, Jan. 1996, pp. 8-5 thru 8-7.

The Kendall Company, The New SCD Compression Sleeve, Aug. 1993, pp. 1-2.

Tyco Healthcare Kendall, Prevention Gets Personal Mar. 2001, pp. 1, 2, 4.

Kendall SCD, Sequential Compression Sleeves, Patent Information, Jan. 1993, 6 pages.

European Exam Report issued in Application No. 06025443.0 dated Sep. 26, 2008, 4 pages.

European Search Report regarding related application serial No. EP 10172794.9 dated Oct. 20, 2010, 5 pages.

European Search Report regarding related application serial No. EP 10177912.2 dated Oct. 15, 2010, 6 pages.

Ramsley and Bushnell, "Development of the US Woodland Battle Dress Uniform", Jan. 1981, p. 8 paragraph 4.

Office action issued Apr. 26, 2011 in related U.S. Appl. No. 12/887,784; 5 pages.

* cited by examiner

COMPRESSION SLEEVE HAVING AIR CONDUITS

CROSS-REFERENCE TO RELATED APPLICATION

This application is a continuation-in-part of U.S. Ser. No. 11/299,488, filed Dec. 12, 2005, the entire contents of that application are incorporated herein by reference.

FIELD OF THE INVENTION

The present disclosure relates generally to a compression sleeve for use in a system for applying compressive forces or pressure to a patient's limb, such as the leg. In particular, the present disclosure relates to a compression sleeve that maintains air flow in the entire sleeve during compression therapy when wrapped around the limb of an individual.

BACKGROUND OF THE INVENTION

Compression devices for applying compressive forces to a selected area of a person's anatomy are generally employed to improve blood flow in the selected area. Compression devices that provide intermittent pulses of a compressed fluid (e.g. air) to inflate at least one inflatable chamber in a sleeve are particularly useful. This cyclic application of pressure provides a non-invasive method of prophylaxis to reduce the incidence of deep vein thrombosis (DVT), and the like. These compression devices find particular use during surgery on patients with high-risk conditions such as obesity, advanced age, malignancy, or prior thromboembolism. Patients who have this condition often have swelling (i.e. edema) and tissue breakdown (i.e. venous stasis ulcer) in the lower leg.

In general, compression devices include a sleeve having at least one fluid inflatable pressure chamber progressively arranged longitudinally along the sleeve. A pressure source (e.g. a pump) is provided for intermittently forming a pressure pulse within these inflatable chambers from a source of pressurized fluid during periodic compression cycles. The compression sleeves provide a pressure gradient along the patient's limbs during these compression cycles, which progressively decreases from the lower portion to the upper portion of the limb (i.e. from the ankle to the thigh).

Examples of compression sleeves are disclosed in U.S. Pat. Nos. 4,013,069 and 4,030,488 to Hasty, U.S. Pat. Nos. 4,029,087 and 5,795,312 to Dye, and U.S. Pat. No. 5,626,556 to Tobler et al., all of which are currently owned by Tyco Healthcare Group, LP and are incorporated by reference herein in their entirety. Other examples of compression sleeves are disclosed in U.S. Pat. Nos. 4,696,289 to Gardner et al. and 5,989,204 to Lina.

When compression therapy is administered to a patient, the inflatable pressure chambers of the compression sleeves of the foregoing description may include trapped air. Trapped air changes the volume of a chamber, thus reducing the pressure gradient along the patient's limb during treatment. The shape, weight, and position of a patient's limb will contribute to the size and number of pockets of air formed. An example of compression treatment method is disclosed in U.S. Pat. No. 6,231,532 to Watson et al., which is currently owned by Tyco Healthcare Group, LP, the contents of which are hereby incorporated by reference herein in their entirety.

SUMMARY OF THE INVENTION

The present disclosure is directed towards a compression sleeve for applying compressive forces or pressure to a selected portion of a patient's anatomy. The compression sleeve includes a sleeve having a plurality of inflatable sections and at least one conduit disposed within one of the plurality of inflatable sections. A plurality of lumens is provided for operatively connecting the sleeve to a controller having a source of pressurized fluid (e.g. air). The compression sleeve further includes hook and loop features attached thereto for securing the compression sleeve to the selected portion of the patient's anatomy.

In one embodiment, the compression sleeve includes a sleeve for applying compressive forces or pressure to a patient's limb (e.g. a leg). The sleeve includes first and second sheets defining a plurality of inflatable sections or chambers, and at least one air conduit disposed within the plurality of inflatable sections. The first and second sheets are fixedly joined by radio frequency (RF) welding, or by other suitable methods, along their corresponding perimeters, thereby defining a plurality of inflatable sections therebetween. The second layer provides the attachment surface for the hook and loop features.

The plurality of inflatable sections is configured for receiving and retaining a pressurized fluid (e.g. air) from a pressurized fluid source for exerting compressive forces or pressure to a portion of the patient's leg during successive pressure applying cycles.

The air conduit is configured and adapted for creating a passage for facilitating the flow of the pressurized air in the plurality of inflatable sections or chambers during compression therapy. When the pressurized air is introduced into each inflatable section, the passage created by the air conduit between the first and second sheets improves the inflation characteristics of each inflatable section. Moreover, the air conduit, during deflation of the compression sleeve, channels the pressurized air towards the fluid source, thereby improving the removal of the pressurized air and minimizing the formation of random pockets of pressurized air.

The air conduit is attached to a top or bottom layer of bladder material. The conduit is positioned within the inflatable area of the bladder. The inflatable area is formed by RF welding or sewing the two sheets together. The conduit may extend along the length or circumferentially around the limb, but within the perimeter as determined by the welding of the two sheets. An inflatable bladder may have one or more conduits within.

Other features of the presently disclosed compression sleeve will become apparent from the following detailed description, taken in conjunction with the accompanying drawings that illustrate, by way of example, the presently disclosed compression sleeve.

The features of the presently disclosed compression sleeve will become more readily apparent by referring to the following detailed description of embodiments, which are described with reference to the drawings.

DETAILED DESCRIPTION OF THE DRAWINGS

Figure 1:
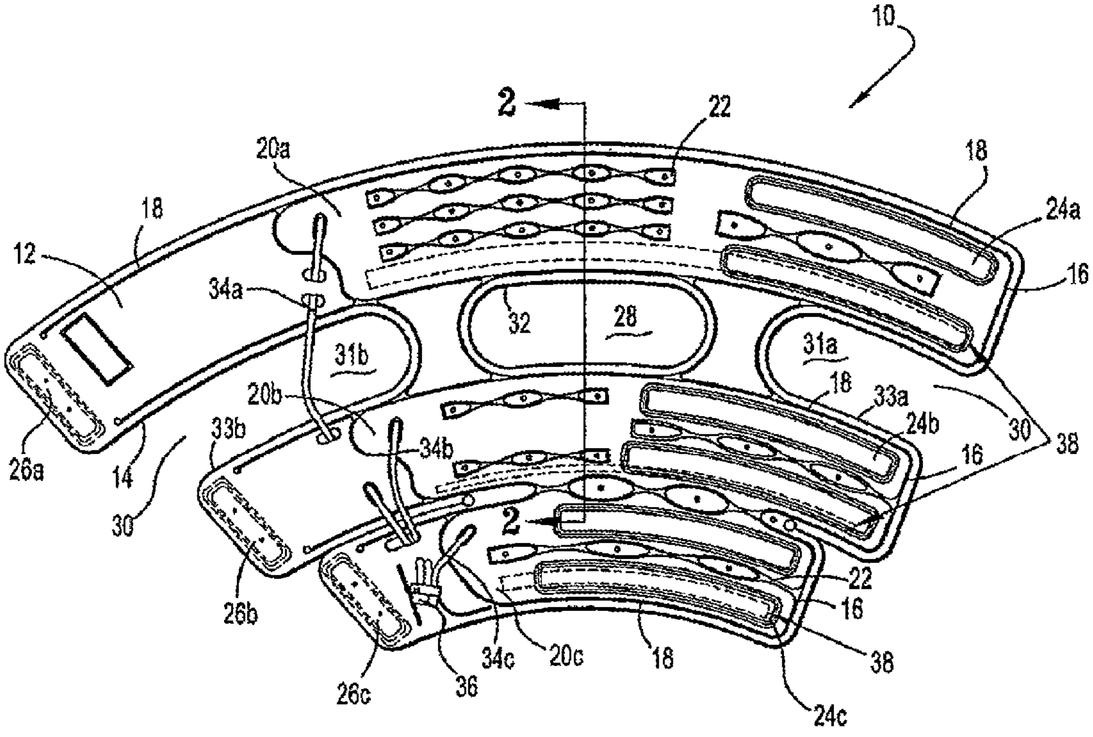
FIG. 1 is a plan view of a compression sleeve, in accordance with the present disclosure.

Referring now to the drawing figures, in which like reference numerals identify identical or corresponding elements, various embodiments of the presently disclosed compression sleeve will now be described in detail. The compression sleeve of the present disclosure is similar to the compression sleeve disclosed in U.S. Pat. Nos. 5,626,556 to Tobler et al. and 5,795,312 to Dye, both of which are currently owned by Tyco Healthcare Group, LP and are incorporated by reference herein in their entirety.

With initial reference to FIG. 1, a compression sleeve in accordance with the present disclosure is illustrated and is designated generally as compression sleeve 10. Compression sleeve 10 is adapted for use in a system for applying compressive forces or pressure to a portion of a patient's limbs such as, for example, the legs. Compression sleeve 10 includes first or outer sheet 12 and second or inner sheet 14 connected by a plurality of laterally extending sealing lines 16 and longitudinally extending sealing lines 18 connecting the ends of lateral sealing lines 16. First and second sheets 12, 14 are adapted as inner gas-impervious sheets, for placement against the person's limbs. Sealing lines 16, 18 may be formed by radio frequency (RF) welding, etc. Moreover, sealing lines 16, 18 define a plurality of longitudinally disposed inflatable sections or chambers 20*a*, 20*b*, and 20*c* which are capable of retaining a pressurized fluid such as, for example, air, in order to exert compressive forces to the patient's limbs during successive pressure-applying cycles.

First sheet 12 may, for example, comprise a suitable flexible polymeric material such as, for example, polyvinyl chloride (PVC) on the order of 5-10 mils thick. Second sheet 14 will preferably comprise a similar polymeric material (i.e. 5-10 mil PVC) having a non-woven material, such as polyester, laminated to the inner surface that is placed against the limb, thereby increasing the comfort of the wearer. Each inflatable section 20*a*, 20*b*, and 20*c* may include at least one wave-shaped border 22. When inflatable sections 20*a*, 20*b*, and 20*c* abut one another, wave-shaped border 22 defines a plurality of un-inflatable "eyes", as illustrated in FIG. 1.

In addition, compression sleeve 10 includes a plurality of hook and loop fasteners for attaching the sleeve about the patient's limb. Hook and loop fasteners include a set of spaced strips 24*a*, 24*b*, and 24*c*, such as loop material positioned on first sheet 12. Strips 24*a*, 24*b*, and 24*c* extend laterally at the inflatable sections 20*a*, 20*b*, and 20*c*, and cooperate with a set of spaced hook materials 26*a*, 26*b*, and 26*c* disposed on second sheet 14 for releasably fastening sleeve 10 to the leg.

When compression sleeve 10 is attached to the patient's limbs, each inflatable section 20*a*, 20*b*, and 20*c* is oriented in a direction that is substantially transverse to a longitudinal axis of the patient's limb. That is, compression sleeve 10 encircles the leg.

Compression sleeve 10 includes an elongated opening 28 extending through what would be the knee region 30 when the sleeve is employed to apply compressive forces or pressure to the limb, opening 28 being defined by peripheral edges 32 extending around the opening. In addition, the knee region 30 has elongated cut-outs or openings 31*a* and 31*b* being defined by peripheral side edges 33*a* and 33*b*, respectively. Compression sleeve 10 is provided with a set of lumens 34*a*, 34*b* and 34*c* having a connector 36 for operably connecting lumens 34*a*, 34*b* and 34*c* to a controller (not shown) having a source of pressurized fluid (e.g. air).

With continued reference to FIG. 1, compression sleeve 10 further includes a plurality of air conduits 38 disposed within at least one of inflatable sections 20*a*, 20*b*, or 20*c*. Air conduit 38 is adapted for creating a passage for facilitating the flow of the pressurized air in the at least one inflatable section 20*a*, 20*b*, or 20*c* when compression therapy is being administered. Each air conduit 38 facilitates the flow of the pressurized air within inflatable sections 20*a*, 20*b*, or 20*c* by separating first and second sheets 12 and 14 when compression sleeve 10 is in a deflated state. Although air conduit 38 is shown as a linear structure in the various figures, air conduit 38 may be shaped to follow an arc that substantially corresponds to the arc defined by inflatable sections 20*a*, 20*b*, or 20*c* (see FIG. 1).

Air conduit 38 may be formed from extruded PVC. It is envisioned that each air conduit 38 may be constructed to fit the shape of other flexible sleeves and foot cuffs such as those available from Kendall's product catalog H-4693VT "Vascular Therapy Products."

In use, compression sleeve 10, in accordance with the present disclosure, is configured to apply compressive forces to a patient's leg. Compression sleeve 10 is positioned about the leg of a patient, wherein hook materials 26*a*, 26*b*, and 26*c* are configured for engaging loop materials 24*a*, 24*b*, and 24*c*. After placement of compression sleeve 10 about a leg of the patient and connecting compression sleeve 10 to pressurized fluid source via connector 36, the controller (not shown) may then be actuated for supplying pressurized air to compression sleeve 10 and initiating compression therapy. Thus, the controller intermittently inflates inflatable sections 20*a*, 20*b*, and 20*c* sequentially during periodic compression cycles and defines a pressure gradient profile.

Air conduit 38 inhibits the formation of random pockets of air in each of the inflatable sections. When the pressurized air is introduced into each inflatable section 20*a*, 20*b*, and 20*c*, the passage created by the at least one air conduit 38 located between first and second sheets 12, 14, improves the inflation characteristics of each inflatable section. In devices that do not include at least one air conduit 38, as inflatable sections 20*a*, 20*b*, or 20*c* deflate, first and second sheets 12, 14 collapse and may form random pockets of pressurized air. These pockets randomly redirect and/or restrict the flow of the pressurized fluid through the inflatable sections 20*a*, 20*b*, or 20*c*, thereby obstructing the removal of the pressurized fluid.

By positioning air conduit 38 within inflatable sections 20*a*, 20*b*, or 20*c*, a passage is created for facilitating the flow of pressurized fluid in each of the inflatable sections 20*a*, 20*b*, or 20*c*. Deflation between successive inflation cycles occurs by returning the air in inflatable sections 20*a*, 20*b*, and 20*c* to the controller or to another vent (not shown), as is known in the art. Air conduit 38 effectively channels the pressurized air towards lumen 34*a*, 34*b*, or 34*c*, thus minimizing the formation of random pockets of pressurized air in each inflatable section 20*a*, 20*b*, or 20*c*. In addition, air conduit 38 channels the pressurized air towards lumens 34*a*, 34*b*, or 34*c* thereby improving the removal rate of the pressurized air and minimizing the formation of random pockets of pressurized air throughout compression sleeve 10.

Figure 2B:
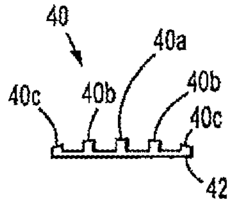
FIGS. 2A-2B are plan and cross-sectional views, respectively, of a first embodiment of an air conduit in accordance with the present disclosure.
Figure 2A:
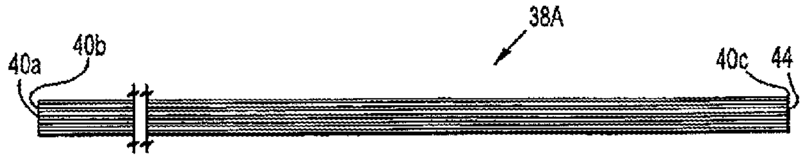
Figure 2C:
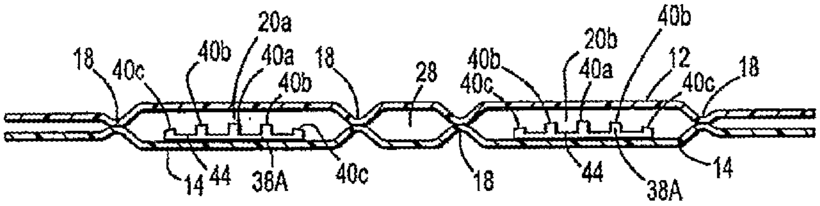
FIG. 2C is a cross-sectional view taken along line 2-2 in FIG. 1, illustrating the air conduit of FIG. 2A positioned within the inflatable sections of the compression sleeve.

With reference to FIGS. 2A-2C, one embodiment of air conduit 38 is illustrated and is designated generally as air conduit 38A. Air conduit 38A includes a plurality of ridges or ribs 40 extruding upwards from a base member 42. Base member 42 is adhesively fastened to second sheet 14 or first sheet 12 of inflatable sections 20*a*, 20*b*, or 20*c*, and ribs 40 are in releasable contact with the first sheet 12 or second sheet 14 of the inflatable section 20*a*, as illustrated in FIG. 2C. The plurality of ribs 40 includes a center rib 40*a*, middle ribs, 40*b*, and outer ribs 40*c* that will be discussed in detail hereinbelow.

With particular reference to FIG. 2B, the height of ribs 40 is at a minimum at the outer edges of base member 42 and progressively increases towards the center of the base member 42 such that center rib 40*a* has the greatest height of ribs 40. Base member has a thickness from about 19 mils to about 39 mils. In one embodiment, center rib has a height from about 65 mils to about 85 mils, middle ribs 40*b* have a height from about 43 mils to about 63 mils, and outer ribs have a height from about 29 mils to about 49 mils. Further still, center rib has a width from about 50 mils to about 70 mils, while middle and outer ribs 40*b* and 40*c* have a width of about 40 mils to about 60 mils. Therefore, air conduit 38 has a low profile and, in combination with first and second sheets 12, 14, defines a low profile compression sleeve 10. Moreover, adjacent middle and outer ribs 40*b* and 40*c*, respectively, are spaced apart defining troughs 44 therebetween. Troughs 44 fluidly couple the opposing ends of air conduit 38A and are configured for channeling the pressurized air within inflatable sections 20*a*, 20*b*, or 20*c* towards lumens 34*a*, 34*b*, or 34*c*. In use, when the pressurized air is introduced into inflatable sections 20*a*, 20*b*, and 20*c*, the passage created by ribs 40 in air conduit 38A improves the inflation characteristics of inflatable sections 20*a*, 20*b*, or 20*c*. During deflation, troughs 44 channel the pressurized air towards lumens 34*a*, 34*b*, or 34*c*, effectively improving the removal of the pressurized air and minimizing the formation of random pockets of pressurized air.

Figure 3B:
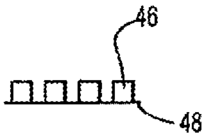
FIGS. 3A-3B are plan and cross-sectional views, respectively, of a second embodiment of the air conduit in accordance with the preset disclosure.
Figure 3A:
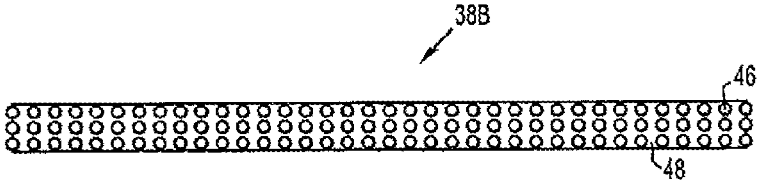
Figure 3C:
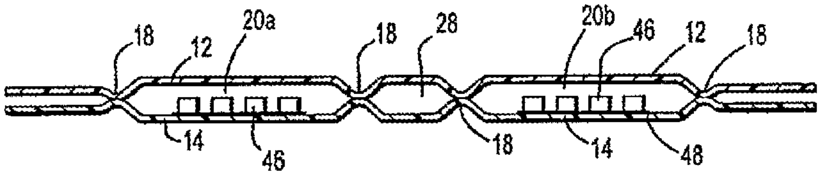
FIG. 3C is a cross-sectional view taken along line 2-2 in FIG. 1, illustrating the air conduit of FIG. 3A positioned within the inflatable sections of the compression sleeve.

With reference to FIGS. 3A, 3B and 3C, a second embodiment of air conduit 38, in accordance with the present disclosure, is illustrated and is designated generally as air conduit 38B. As best illustrated in FIG. 3B, air conduit 38B includes a plurality of randomly placed pins or knobs 46 extending upward from a base member 48. Base member 48 is fastened to second sheet 14 or first sheet 12 of inflatable sections 20*a* 20*b*, or 20*c* and pins 46 are in releasable contact with first sheet 12 or second sheet 14 of at least one of inflatable sections 20*a*, 20*b*, or 20*c*, as illustrated in FIG. 3C. Thus, air conduit 38B effectively separates first and second sheets 12 and 14 when compression sleeve 10 is in a deflated state. The passage created by the plurality of pins 46 improves the inflation characteristics of inflatable sections 20*a*, 20*b*, or 20*c*. During deflation, pins 46 channel the pressurized air towards lumens 34*a*, 34*b*, or 34*c*, effectively improving the removal of the pressurized air and minimizing the formation of random pockets of pressurized air.

Figure 4B:
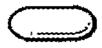
FIGS. 4A-4B are plan and cross-sectional views, respectively, of yet another embodiment of the air conduit in accordance with the preset disclosure.
Figure 4A:
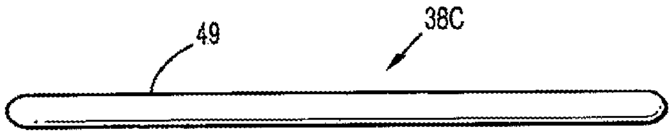
Figure 4C:
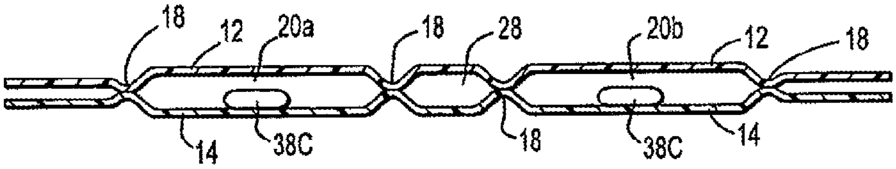
FIG. 4C is a cross-sectional view taken along line 2-2 in FIG. 1, illustrating the air conduit of FIG. 4A positioned within the inflatable sections of the compression sleeve.

With reference to FIGS. 4A-4C, another embodiment of air conduit 38 is illustrated and is designated generally as air conduit 38C. Air conduit 38C includes at least one inflatable elongated sheath 49 positioned within at least one of inflatable sections 20*a*, 20*b*, or 20*c*. The at least one elongated sheath 49 is adhesively fastened to second sheet 14 or first sheet 12 and is in releasable contact with first sheet 12 or second sheet 14, as illustrated by FIG. 4C. In an alternative embodiment, the sheath may be RF welded to an inside surface of second sheet 14 or first sheet 12. In this particular embodiment, air conduit 38C forms a circumferential bubble passageway, as illustrated in FIG. 4C. The at least one elongated sheath 49 may be formed from a foam material wherein the foam material does not collapse under the load of the leg, thus maintaining a separation between first and second sheets 12 and 14. In use, when the pressurized air is introduced into inflatable sections 20*a*, 20*b*, and 20*c*, the circumferential bubble passageway formed by air conduit 38C improves the inflation characteristics of inflatable sections 20*a*, 20*b*, or 20*c*. During deflation, the at least one elongated sheath 49 channels the pressurized air towards lumens 34*a*, 34*b*, or 34*c*, effectively improving the removal of the pressurized air and minimizing the formation of random pockets of pressurized air. In addition, elongated sheath 49 may also be positioned on the outer surface of first and second sheets 12 and 14 for providing a rigid support structure of the sleeve for receiving the leg. Alternatively, a separate leg support may be provided to keep the limb raised off the bed surface.

Figure 5B:
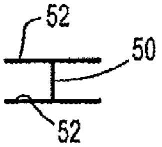
FIGS. 5A-5B are plan and cross-sectional views, respectively, of yet another embodiment of the air conduit in accordance with the preset disclosure.
Figure 5A:
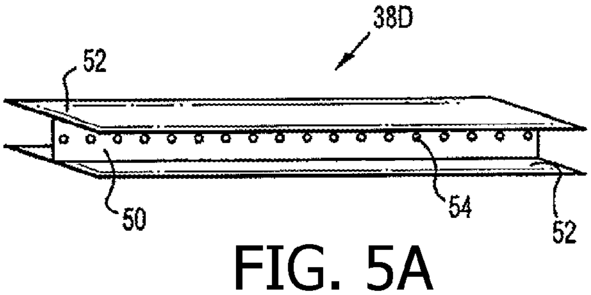
Figure 5C:
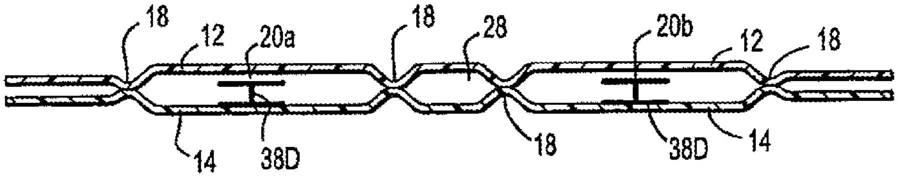
FIG. 5C is a cross-sectional view taken along line 2-2 in FIG. 1, illustrating the air conduit of FIG. 5A positioned within the inflatable sections of the compression sleeve.

With reference to FIGS. 5A, 5B and 5C, yet another embodiment of air conduit 38 is illustrated and is designated generally as air conduit 38D. Air conduit 38D is similar to air conduit 38A and will only be discussed in detail to the extent necessary to identify differences in construction and operation. Air conduit 38D includes a semi-rigid "I" beam having a web 50 and two flange portions 52 disposed on either end of web 50. Air conduit 38D is positioned within at least one of inflatable sections 20*a*, 20*b*, or 20*c* in a manner illustrated in FIG. 5C for separating first and second sheets 12 and 14, thus preventing sleeve 10 from collapsing under the weight of the patient's leg. In addition, a plurality of openings 54 is disposed on web 50 for facilitating communication throughout inflatable sections 20*a*, 20*b*, or 20*c*. In use, when the pressurized air is introduced into inflatable sections 20*a*, 20*b*, or 20*c*, the plurality of openings 54 disposed on web 50 improves the inflation characteristics of inflatable sections 20*a*, 20*b*, or 20*c*. During deflation, the semi-rigid "I" beam of air conduit 38D channels the pressurized air towards lumens 34*a*, 34*b*, or 34*c*, effectively improving the removal of the pressurized air and minimizing the formation of random pockets of pressurized air.

Figure 6B:
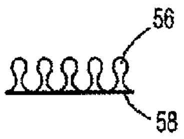
FIGS. 6A-6B are plan and cross-sectional views, respectively, of yet another embodiment of the air conduit in accordance with the preset disclosure.
Figure 6A:
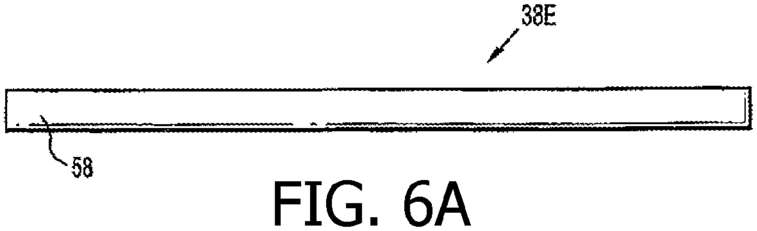
Figure 6C:
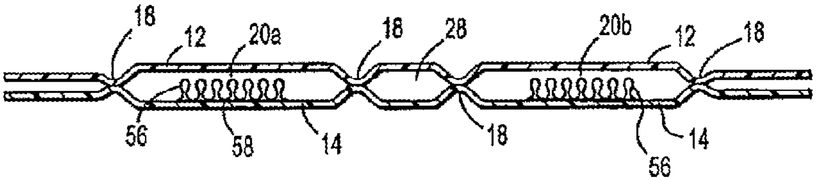
FIG. 6C is a cross-sectional view taken along line 2-2 in FIG. 1, illustrating the air conduit of FIG. 6A positioned within the inflatable sections of the compression sleeve.

With reference to FIGS. 6A-6C, yet another embodiment of air conduit 38 is illustrated and is designated generally as air conduit 38E. Air conduit 38E is similar to air conduit 38A and will only be discussed in detail to the extent necessary to identify differences in construction and operation. Air conduit 38E includes a plurality of longitudinal corrugated extrusions 56 attached to base 58. Corrugated extrusions 56 form a passageway for air to pass therethrough. It is envisioned that corrugated extrusions 56 will permit air to infiltrate into inflatable sections 20*a*, 20*b*, or 20*c*. In use, when the pressurized air is introduced into inflatable sections 20*a*, 20*b* and 20*c*, the corrugated extrusions 56 improves the inflation characteristics of inflatable sections 20*a*, 20*b*, or 20*c*. During deflation, the corrugated extrusions channel the pressurized air towards lumens 34*a*, 34*b*, or 34*c*, effectively improving the removal of the pressurized air and minimizing the formation of random pockets of pressurized air.

Figure 7B:
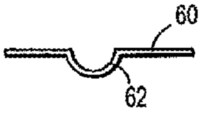
FIGS. 7A-7B are plan and cross-sectional views, respectively, of yet another embodiment of the air conduit in accordance with the preset disclosure.
Figure 7A:
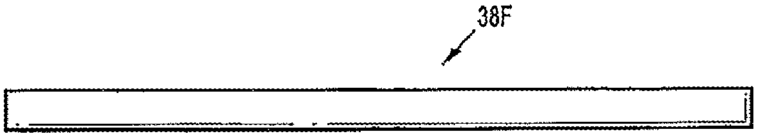
Figure 7C:
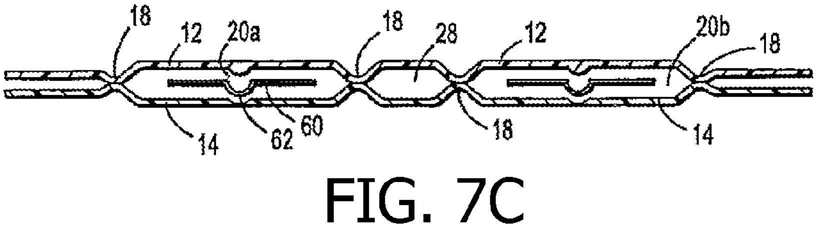
FIG. 7C is a cross-sectional view taken along line 2-2 in FIG. 1, illustrating the air conduit of FIG. 7A positioned within the inflatable sections of the compression sleeve.

With reference to FIGS. 7A-7C, yet another embodiment of air conduit 38 is illustrated and is designated generally as air conduit 38F. Air conduit 38F is similar to air conduit 38A and will only be discussed in detail to the extent necessary to identify differences in construction and operation. Air conduit 38F includes a base portion 60 having a central longitudinal channel 62, as illustrated in FIG. 7B. In this particular embodiment, air conduit 38F is installed within inflatable sections 20*a*, 20*b*, or 20*c* such that channel 62 forms a passageway therethrough. Base portion 60 and channel 62 may be inflatable or, alternatively, may be RF welded onto first and second sheets 12, 14. They may also be reinforced with an additional layer of PVC sheet to form a more rigid conduit. In use, when the pressurized air is introduced into inflatable sections 20*a*, 20*b*, and 20*c*, central longitudinal channel 62 improves the inflation characteristics of inflatable sections 20*a*, 20*b*, or 20*c*. During deflation, longitudinal channel 62 directs the pressurized air towards lumens 34*a*, 34*b*, or 34*c*, effectively improving the removal of the pressurized air and minimizing the formation of random pockets of pressurized air.

Figure 7D:
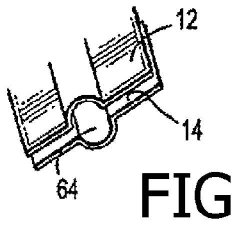
FIG. 7D is a front elevational view of the compressive sleeve showing a linear void across the sleeve.

Alternatively, first and second sheets 12, 14 may be RF welded, having a pre-fabricated feature, wherein a linear void 64 across the sleeve is formed, as illustrated in FIG. 7D. In this particular embodiment, linear void 64 directs the pressurized air towards lumen 34*a*, 34*b*, and 34*c* for improving the removal of the pressurized air and minimizing the formation of random pockets of pressurized air.

Figure 8B:
FIGS. 8A-8B are plan and cross-sectional views, respectively, of yet another embodiment of the air conduit in accordance with the preset disclosure.
Figure 8A:
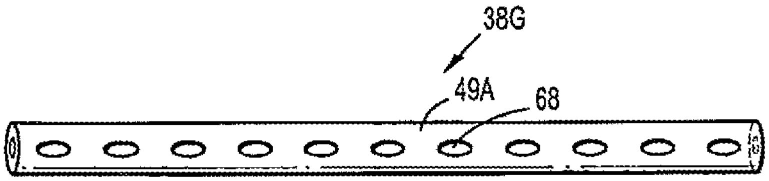
Figure 8C:
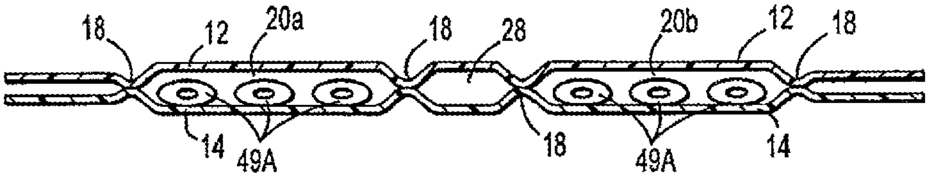
FIG. 8C is a cross-sectional view taken along line 2-2 in FIG. 1, illustrating the air conduit of FIG. 8A positioned within the inflatable sections of the compression sleeve.

With reference to FIGS. 8A, 8B and 8C, yet another embodiment of air conduit 38 is illustrated and is designated generally as air conduit 38G. Air conduit 38G is similar to air conduit 38C (FIGS. 4A, 4B and 4C) and will only be discussed in detail to the extent necessary to identify differences in construction and operation. Air conduit 38G includes at least one elongated sheath 49A having an axial aperture 66 (FIG. 8B) and a plurality of transverse openings 68 (FIG. 8A). Axial aperture 66 and transverse openings 68 permit air to disperse across the full length of compression sleeve 10. The at least one elongated sheath 49A may be positioned within inflatable sections 20*a*, 20*b*, or 20*c*, adhesively fastened to second sheet 14 or the first sheet 12 and in releasable contact with first sheet 12 or second sheet 14, as illustrated in FIG. 8C. In use, when the pressurized air is introduced into inflatable sections 20*a*, 20*b*, and 20*c*, axial aperture 66 and transverse openings 68 of the at least one elongated sheath 49A improves the inflation characteristics of inflatable sections 20*a*, 20*b*, or 20*c*. During deflation, axial aperture 66 channels the pressurized air towards lumens 34*a*, 34*b*, or 34*c*, effectively improving the removal of the pressurized air and minimizing the formation of random pockets of pressurized air.

Figure 9:
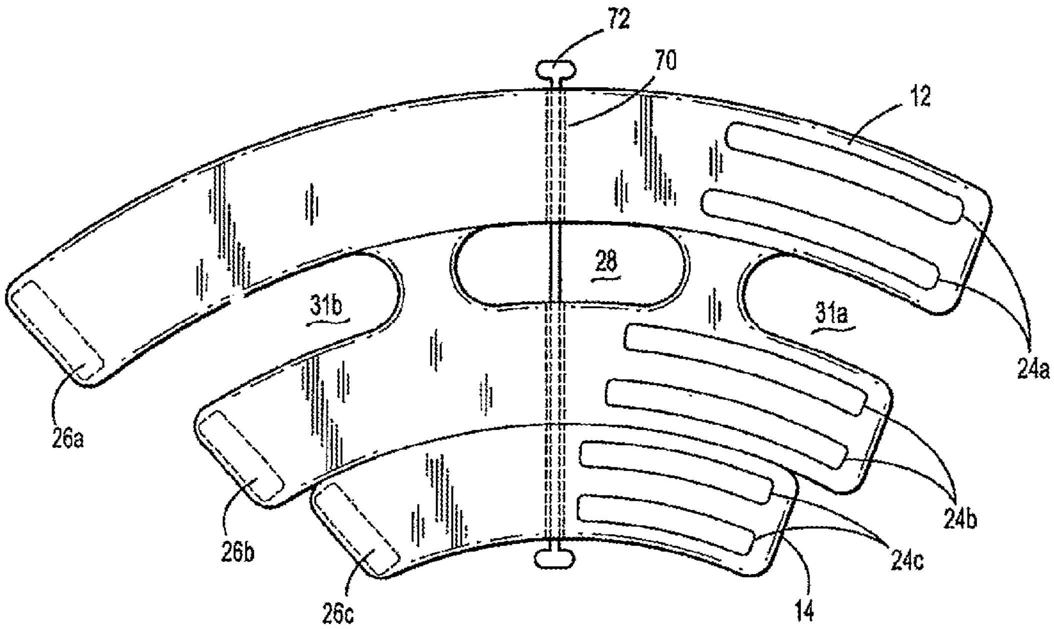
FIG. 9 is a plan view of the compression sleeve illustrating yet another embodiment of the air conduit in accordance with the present disclosure.

Other methods of facilitating the flow of pressurized air within inflatable sections 20*a*, 20*b*, and 20*c* are envisioned. For example, compression sleeve 10 may be manufactured to include a channel 70 for sliding a support member 72 therethrough, as illustrated in FIG. 9, for providing a rigid support structure to compression sleeve 10. Thus, support member 72 will rigidly support the weight of the leg. Alternatively, sealing lines 16 (FIG. 1) may be strategically placed along first and second sheets 12, 14 for facilitating the passage of air. Moreover, inflatable sections 20*a*, 20*b*, and 20*c* may be filled with styrene foam pellets for adding structural rigidity and still permitting the flow of pressurized air throughout inflatable sections 20*a*, 20*b*, and 20*c*. In addition, a plurality of connectors 36 may be strategically installed throughout the compression sleeve for supplying inflatable sections 20*a*, 20*b*, and 20*c* with pressurized air from a plurality of points. Likewise, the plurality of connectors 36 can be actuated to deflate a chamber to minimize air pockets. Moreover, the strength of the sleeve material may be increased in order to allow for increased burst strength, permitting more pressure and volume to raise the large limb. For example, first and second sheets 12, 14 may be formed from a rigid material to prevent inflatable sections 20*a*, 20*b*, and 20*c* from collapsing under the weight of a large limb. Moreover, during manufacture of compression sleeve 10, a plurality of passageways may be embossed along the surface of first and second sheets 12, 14.

Figure 10A:
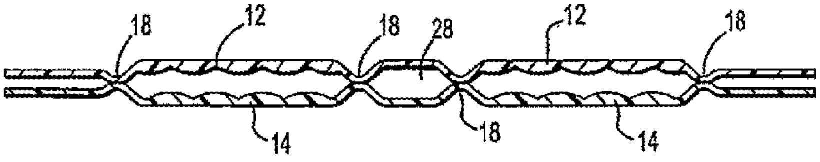
FIGS. 10A-B are cross-sectional views of another embodiment of the compression sleeve illustrating various textures of an inner surface of first and second sheets in accordance with the present disclosure.
Figure 10B:
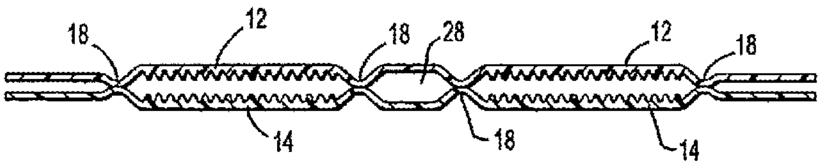

With reference to FIGS. 10A and 10B, first and second sheets 12, 14 may include a design or feature wherein the texture of the sleeve improves the flow of air. For example, particular textures may be provided on an inside surface of first and second sheets 12, 14, as shown in FIGS. 10A and 10B, such that they never collapse fully, thus facilitating the passage of the pressurized air. The texture may be laminated or may form part of first and second sheets 12 and 14. In use, when the pressurized air is introduced into inflatable sections 20*a*, 20*b*, and 20*c*, the texture on the inside surface of first and second sheets 12 and 14 improves the inflation characteristics of inflatable sections 20*a*, 20*b*, and 20*c*. During deflation, the textures on the inside surface of first and second sheets 12 and 14 assist in channeling the pressurized air towards lumens 34*a*, 34*b*, and 34*c*, effectively improving the removal of the pressurized air and minimizing the formation of random pockets of pressurized air. One skilled in the art will recognize other fluids besides air can be used without departing from the scope of the invention.

Figure 11A:
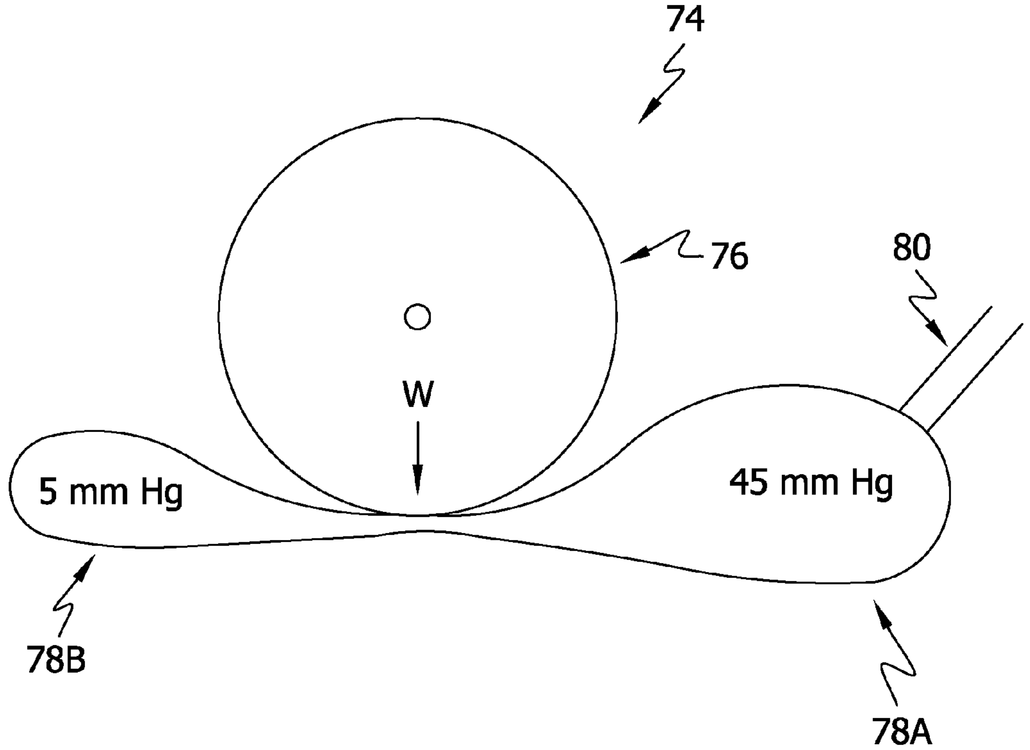
FIG. 11A is a cross-sectional view of a prior alt bladder under the weight of a patient's limb without an air conduit according to one of the embodiments of this invention.
Figure 11B:
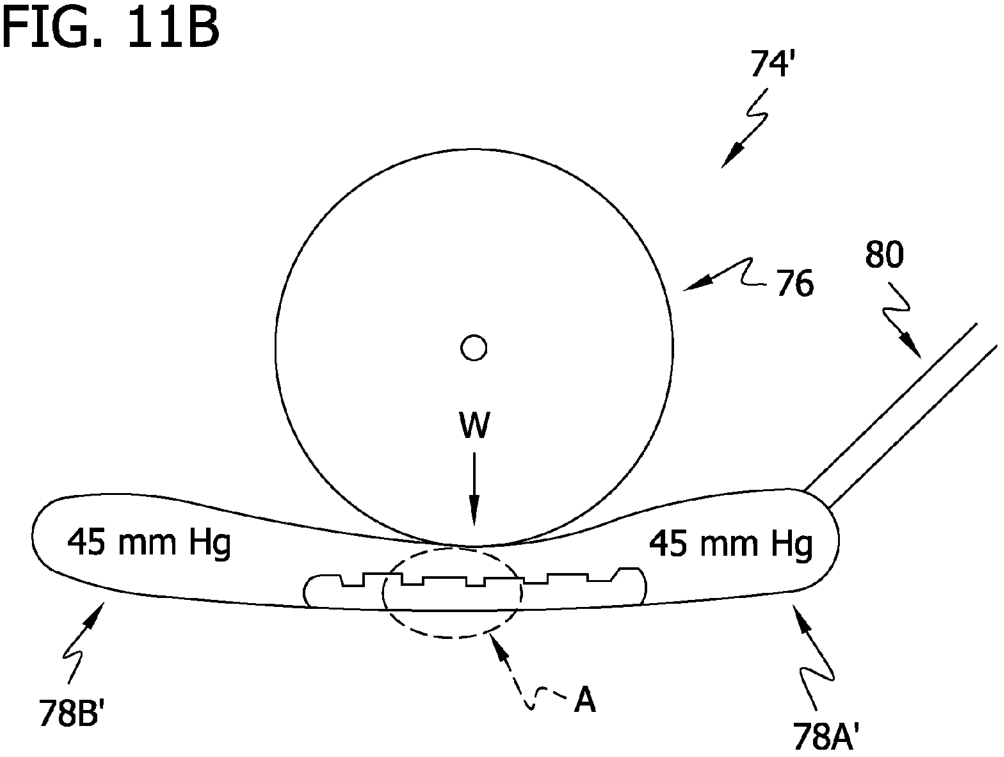
FIG. 11B is a cross-sectional view of a bladder incorporating one of the air conduit embodiments, at A, of this invention

With reference to FIGS. 11A and 11B, a patient's limb 76 can, unfortunately, weight as much as 50 lbs. The leg is typically heavy and broad for those patients with medical conditions related to obesity. An obese leg resting on a leg sleeve bladder is generally shown at FIG. 11A, without the air conduit of the present invention. This prior art configuration

74, shows the sleeve laying flat, as opposed to being circumferentially wrapped about the limb. Opposing tabs (not shown) are positioned along the longitudinal edge, that when the sleeve is wrapped around the limb, the opposing tabs are connected by various means—snaps, belt and buckle, or loop and hook material.

One can see that the therapy pressure 78A, 78B is not evenly distributed around the limb, because the weight "W", of a patient's limb, causes sheets 12, 14 of the bladder to become compressed, constricting or cutting off air flow. As a result of this restriction, the pressure on the port side of the bladder 78A is much higher than its opposite side 78B. This reduces, if not eliminates, therapy, to one side of the limb. Blood will tend to pool in the lower pressure side of the limb. The impact of these devices is to help move blood toward the heart in an effort, among other things, to help remove fluid build up in the limbs.

Figure 12A:
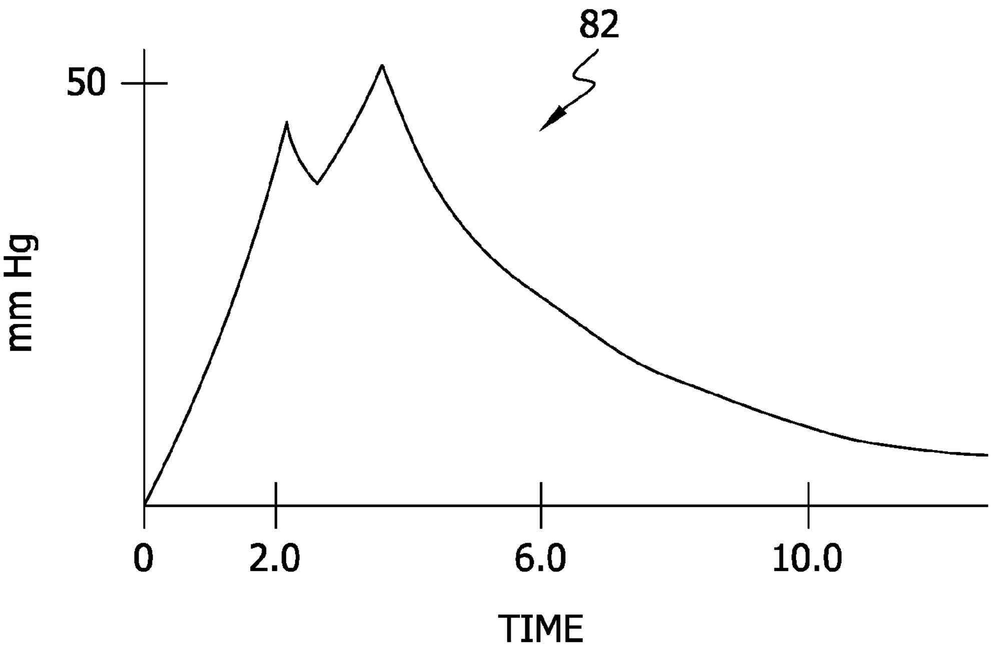
FIG. 12A is a graphical representation of a pressure profile of the bladder shown in FIG. 11A.
Figure 12B:
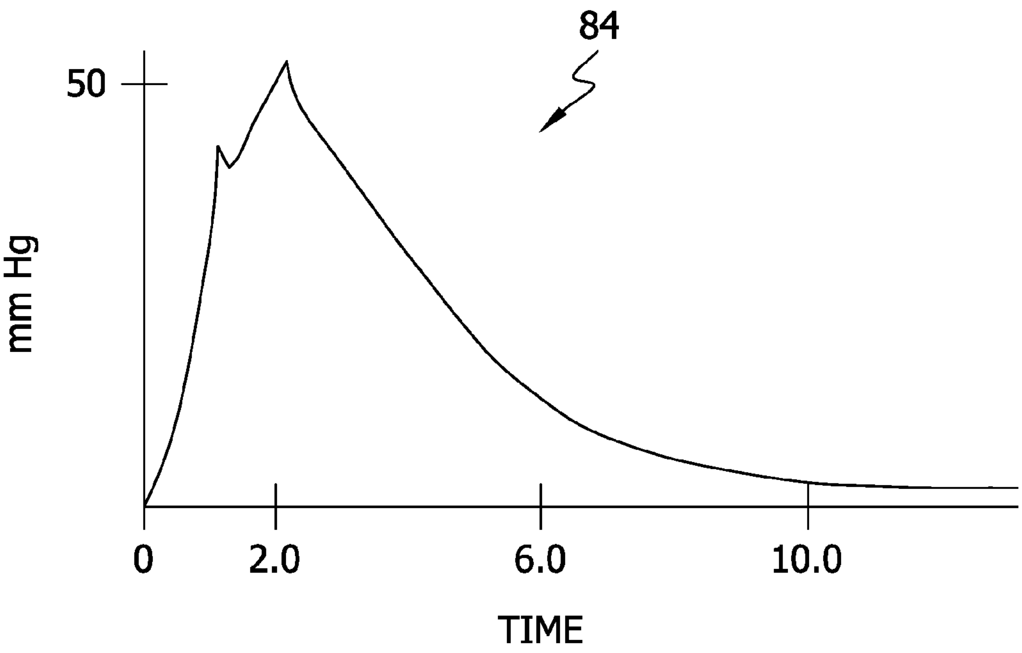
FIG. 12B is a graphical representation of a pressure profile of the bladder shown in FIG. 11B.

The therapy provided is in the form of repeated inflation and deflation of the bladder, generally called a compression cycle. A compression cycle is shown at FIG. 12A, for the prior art device with a heavy limb. The pressure measurement rises to above 50 mmHg. The pressure in a bladder is not fully decayed or removed until sometime after 10 sec. By contrast, FIG. 12B (illustrating the present invention), shows a more rapid inflation and, a more fully decayed bladder in about 6 sec. This allows for a more complete compression cycle, because of a more fully evacuated bladder in a cycle. Also, more therapy cycles are provided for each minute of treatment, in addition to a more complete evacuation of air within the chambers of a bladder. The more complete the cycle of inflation and deflation and a more even distribution of pressure around the limb during a cycle, the more evenly the blood and fluids therein are moved toward the heart. By analogy, the squeezing a tube of toothpaste unevenly along its length, results in pockets of paste. The user then must apply a fairly even force to move the trapped paste toward the opening, by pressing two fingers together along the length of the tube. Other techniques are possible, but the uneven trapping of the paste is analogous to uneven trapped air in the bladder. The folds created by the limb weight) prevent air from being evenly distributed and then evenly evacuated during deflation. This unevenness results in less treatment for larger patients. As with the toothpaste analogy, material, in this case air, is left behind, interfering with the treatment. Large amounts of trapped air must be moved by next inflation cycle resulting in lost energy to move blood.

Figure 13:
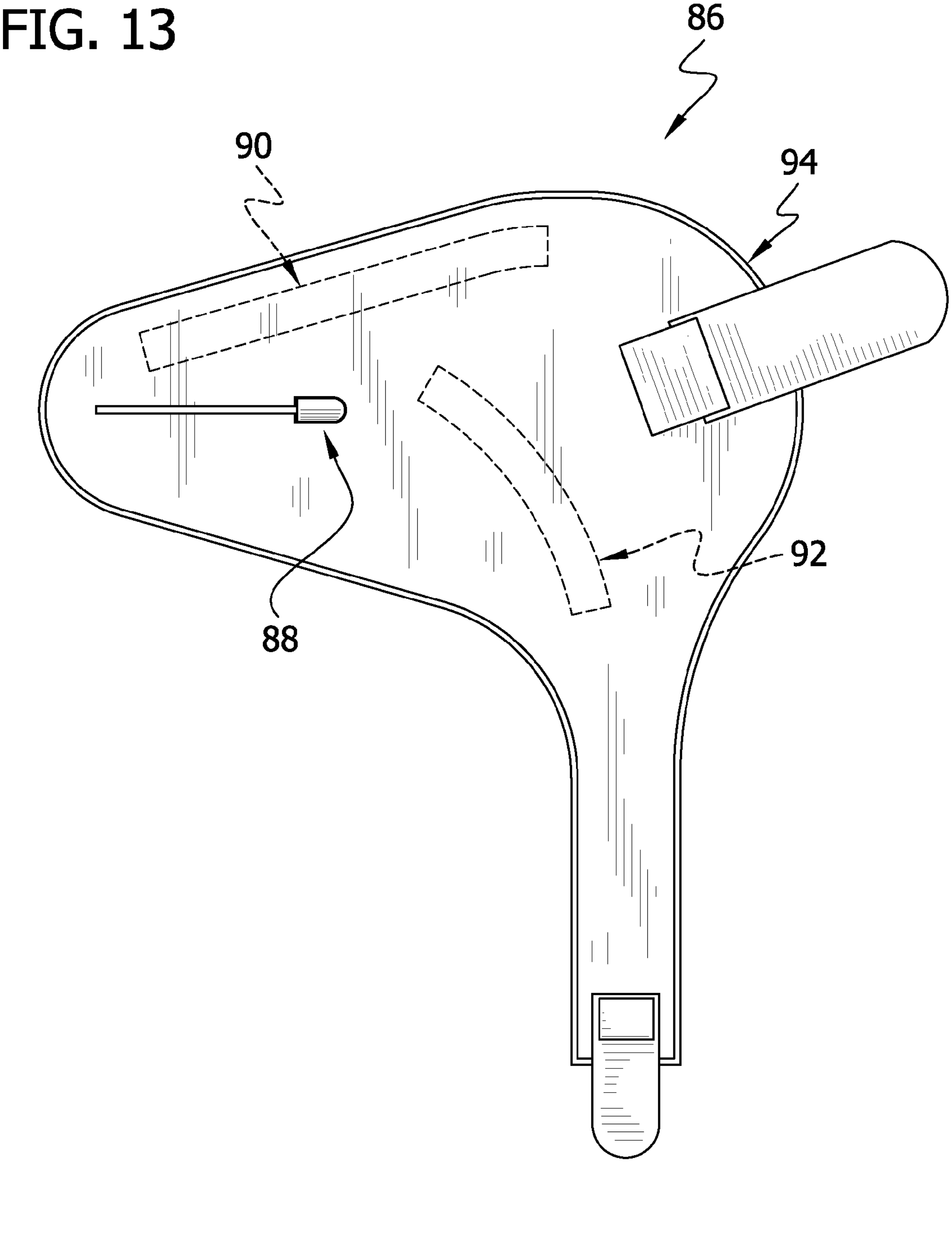
FIG. 13 is a plan view of a foot cuff bladder with air conduits.

FIG. 11B shows an even distribution of air pressure 78A' and 78B' around the limb when the air conduits depicted in FIGS. 2-8 and 10, are used at "A" in FIG. 11A. The air conduit maintains separation of the sheets 12, 14 during a cycle, so pressurized air can flow around the limb. A more even distribution of circumferential pressure around the limb causes more blood to be pushed from the blood vessels nearer the surface of the skin, toward the main vessels within the limb; toward the heart. The more even the pressure about the limb, the more effective the treatment. FIG. 13 shows a plan view of an air conduit within the boundary of a foot cuff bladder 86.

Figure 14:
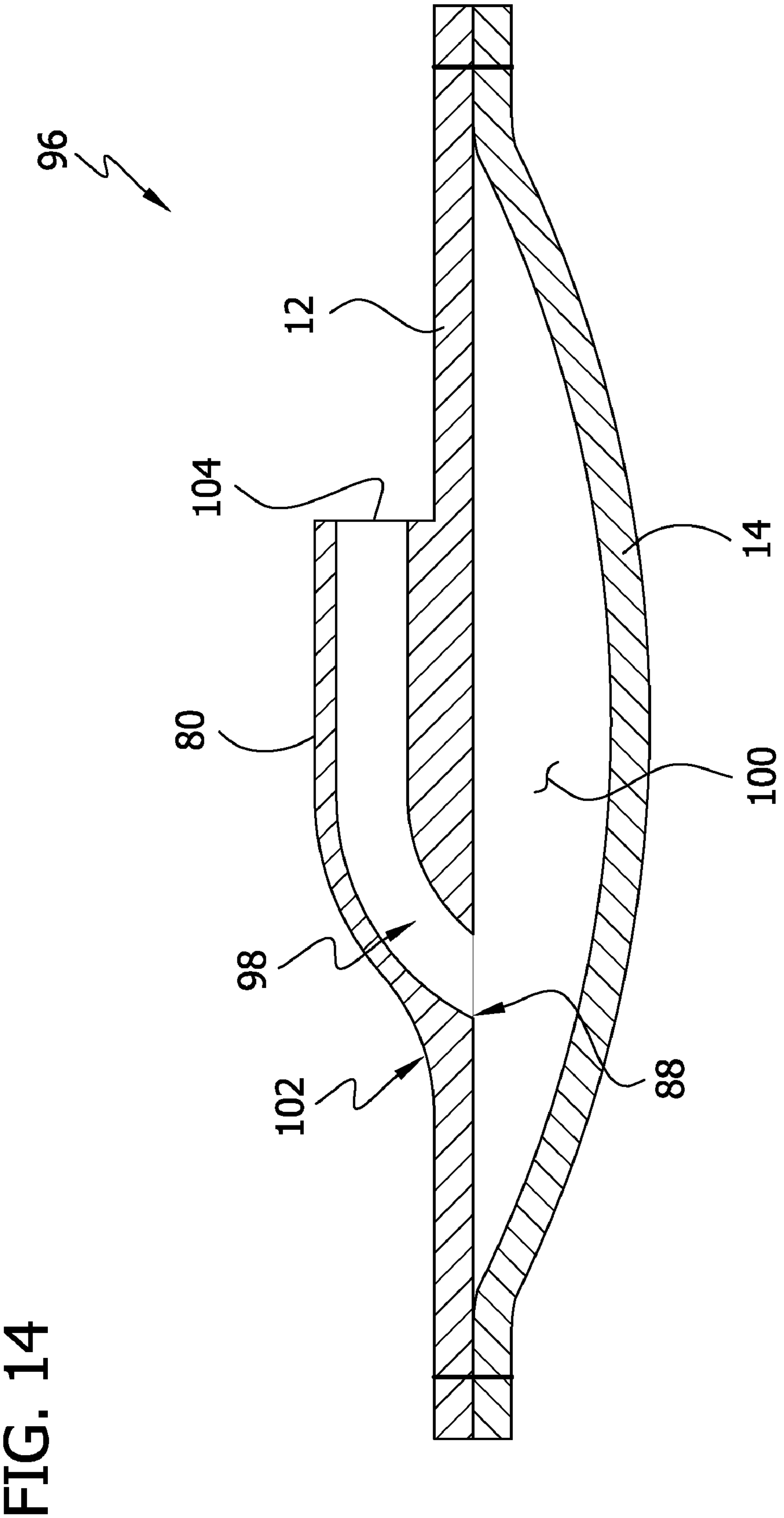
FIG. 14 is a plan view of an inflatable section with a flush mounted or formed lumen.

The foot cuff bladder 86 has a pair of air conduits 90, 92 disposed within a boundary 94 formed at a perimeter of the bladder 100 (FIG. 14). A flush-mounted port 88 provides pressurized air to the bladder 100 (sometimes called an inflatable section). The conduits 90, 92 also help channel the air throughout the bladder 100, and likewise, assist in air evacuating from the bladder 100 during the deflation cycle. The conduit 90, 92 is placed substantially along a dimension of the sheet that forms the inflatable bladder. The conduit 90, 92 is secured to the first or second sheet. The conduit is completely within the boundary of inflatable section and does not extend through the boundary or the surface of the sheet. A foot cuff 86 is similar to a sleeve, except, a foot cuff typically has a one chamber bladder, whereas, a sleeve has one or more bladders along its longitudinal length, and the bladder may have more than one chamber. A chamber is formed using a welding die that clamps together with a pair of sheets therebetween and, with RF energy, causes the first and second sheets of the bladder to melt together to form the air-tight boundary. Within one or more of the chambers may be disposed one or more air conduits, within the boundary of a chamber.

FIG. 14 illustrates a single-chamber bladder 100 with a lumen 80 mounted flush 88 with the first sheet or second sheet 12, 14. The lumen 80, at a first end 98, is mounted flush with an outside surface of the sheet 12, 14. As shown at FIG. 14, the lumen 80 does not extend beyond the surface into the inflatable area 100 formed by the sheets 12, 14. A flange 102, formed as part of the first sheet, provides fluid communication to a pressure source 104 to a first end 98 of the lumen. The pressurized fluid source 104 is capable of inflating and deflating the bladder. This non-limiting embodiment shows one way to flush mount the lumen securely without the lumen extending into the inflatable section.

It will be understood that numerous modifications and changes in form and detail may be made to the embodiments of the present disclosure. For example, it is contemplated that numerous other configurations of the conduit may be used, and the material of the sleeve and/or conduit may be selected from numerous materials, other than those specifically disclosed. Therefore, the above description should not be construed as limiting, but merely as exemplifications of the various embodiments.

What is claimed is:

1. A compression sleeve, comprising:

a first sheet;

a second sheet attached to said first sheet and defining at least one inflatable section;

at least one conduit fixed to the first or second sheet, and the at least one conduit is entirely within a boundary forming the inflatable section and the conduit is substantially along at least one dimension of the inflatable section;

a lumen defined separately from the conduit connected to a source of pressurized fluid; and at a first end of the lumen the lumen is flush mounted with the first or second sheet.

2. The compression sleeve as recited in claim 1, wherein the sleeve comprises a plurality of fasteners comprising hook and loop fastener components adapted for securing the sleeve about a portion of a patient's body.

3. The compression sleeve as recited in claim 1 wherein the at least one conduit includes a base member and a plurality of ridges attached to a first surface of the base member.

4. The compression sleeve as recited in claim 3 wherein the height of the plurality of ridges is a minimum at an outer edge of the base member and at a maximum at a central portion of the base.

5. A method for applying pressure to a portion of a patient's body, comprising the steps of:

attaching a sleeve to the portion of the patient's body, the sleeve including a first sheet, a second sheet attached to said first sheet and defining at least one inflatable section, and at least one conduit disposed entirely in the at least one inflatable section;

connecting a lumen defined separately from the conduit to a source of pressurized fluid, wherein the first or second sheet is formed flush around a first end of the lumen;

inflating the sleeve to a pressure, wherein the at least one conduit creates a passage for facilitating the flow of the pressurized fluid; and deflating the sleeve, wherein a portion of the at least one conduit channels pressurized fluid towards the lumen.

6. The compression sleeve as recited in claim 5 wherein the at least one conduit includes a base member and a plurality of ridges attached to a first surface of the base member.

* * * * *